United States Patent [19]

Schwamborn et al.

[11] Patent Number: 4,640,923
[45] Date of Patent: Feb. 3, 1987

[54] METHODS OF COMBATTING FUNGI EMPLOYING 2,4-DIAMINO-6-HALOGENO-5-ALKYLTHIO-PYRIMIDINES

[75] Inventors: Michael Schwamborn, Cologne; Engelbert Kühle, Bergisch-Gladbach; Erich Klauke, Odenthal; Ludwig Eue, Leverkusen; Robert R. Schmidt, Bergisch-Gladbach; Hans-Joachim Santel, Cologne; Gerd Hänssler, Leverkusen, all of Fed. Rep. of Germany

[73] Assignee: Bayer Aktiengesellschaft, Leverkusen, Fed. Rep. of Germany

[21] Appl. No.: 816,936

[22] Filed: Jan. 8, 1986

Related U.S. Application Data

[62] Division of Ser. No. 730,939, May 3, 1985.

[30] Foreign Application Priority Data

May 10, 1984 [DE] Fed. Rep. of Germany ....... 3417264

[51] Int. Cl.[4] ............................................. A01N 43/54
[52] U.S. Cl. ......................................................... 514/272
[58] Field of Search ............................................ 514/272

[56] References Cited

U.S. PATENT DOCUMENTS 3,843,656 10/1974 Obelliane et al. .................... 544/298
3,968,214 7/1976 Claverie et al. ...................... 544/298
4,051,244 9/1977 Mattioda et al. ..................... 544/298
4,166,852 9/1979 Loiseau et al. ....................... 544/298
4,528,026 7/1985 Balde et al. .............................. 71/92

FOREIGN PATENT DOCUMENTS 0000681 2/1979 European Pat. Off. .
2119234 8/1972 France .

OTHER PUBLICATIONS

Claverie et al., C.A. vol. 83, #202606f, (1975).

Primary Examiner—Allen J. Robinson
Attorney, Agent, or Firm—Sprung Horn Kramer & Woods

[57] ABSTRACT 2,4-Diamino-6-halogeno-5-alkylthio-pyrimidines of the general formual (I)

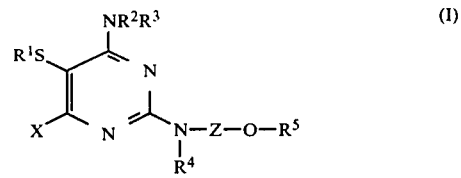

in which
X represents halogen,
$R^1$ represents alkyl which is optionally substituted by halogen,
$R^2$ represents hydrogen or alkyl,
$R^3$ represents hydrogen, alkyl or alkoxyalkyl,
$R^4$ represents hydrogen or alkyl,
Z represents a branched or straight-chain alkylene group and
$R^5$ represents alkyl, process for their preparation and their use as plant protecting agent, particularly as herbicides and fungicides.

6 Claims, No Drawings

METHODS OF COMBATTING FUNGI EMPLOYING 2,4-DIAMINO-6-HALOGENO-5-ALKYLTHIO-PYRIMIDINES

This is a division of application Ser. No. 730,939, filed May 3, 1985, now pending.

The present invention relates to new 2,4-diamino-6-halogen-5-alkylthio-pyrimidines, processes and new intermediates for their preparation and their use as plant protection agents, in particular as herbicides and fungicides.

It is already known that certain 2,4-diamino-6-chloro-5-alkylthio-pyrimidines can be used as herbicides (compare European Pat. No. A-0,000,681). Thus, for example, 2,4-diamino-6-chloro-5-methylthio-pyrimidine can be used as a selective herbicide in cereals, maize, rice and sorghum by the pre-emergence and post-emergence method; however, its action on various harmful plants is not satisfactory when low amounts are applied.

The abovementioned group of compounds is also said to have a certain fungicidal activity (compare French Pat. No. A-2,119,234), but the activity proves to be inadequate against a number of fungal diseases under conditions in practice. In particular, nothing is known of an action of these compounds against Pyricularia oryzae on rice.

New 2,4-diamino-6-halogeno-5-alkylthio-pyrimidines of the general formula (I)

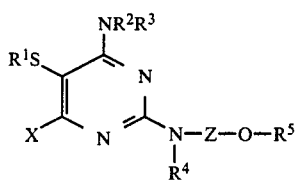

in which
X represents halogen,
$R^1$ represents alkyl which is optionally substituted by halogen,
$R^2$ represents hydrogen or alkyl,
$R^3$ represents hydrogen, or alkoxyalkyl,
$R^4$ represents hydrogen or alkyl,
Z represents a branched or straight-chain alkylene group and
$R^5$ represents alkyl,
have now been discovered.

It has furthermore been found that the pyrimidine derivatives of the general formula (I) are obtained when trihalogenopyrimidines of the general formula (II)

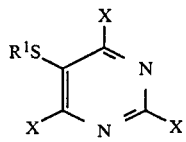

in which
$R^1$ and X have the abovementioned meaning, are either
(A) first reacted (1st stage) with an alkoxyalkylamine of the formula (III)

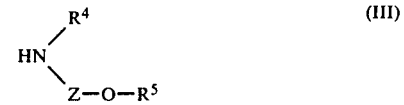

wherein
$R^4$, Z and $R^5$ have the abovementioned meaning, in the presence of an acid-binding agent and if appropriate in the presence of a diluent, to give a mixture of the isomeric pyrimidine derivatives of the general formulae (IVa) and (IVb)

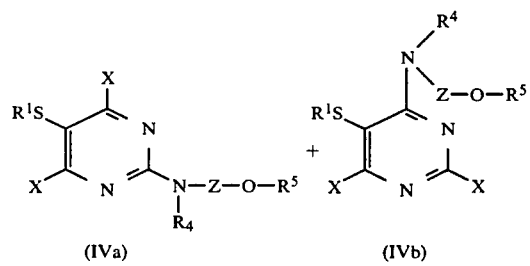

'wherein
$R^1$, X, $R^4$, Z and $R^5$ have the abovementioned meaning, and, after separation of the two isomers, the pyrimidine derivative of the formula (IVa) is then reacted (2nd stage) in a further reaction step with an amine of the formula (V)

'wherein
$R^2$ and $R^3$ have the abovementioned meaning, in the presence of an acid-binding agent and if appropriate in the presence of a diluent, to give the pyrimidine derivative of the formula (I), or
(B) first reacted (1st stage) with an amine of the formula (V)—under the same reaction conditions as in process (A)—to give a mixture of the isomeric pyrimidine derivatives of the general formulae (VIa) and (VIb)

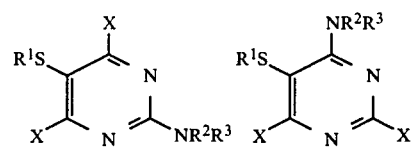

'wherein
$R^1$, X, $R^2$ and $R^3$ have the abovementioned meaning, and, after separation of the two isomers, the pyrimidine derivative of the formula (VIb) is then reacted (2nd stage) in a further reaction stage with an alkoxyalkylamine of the formula (III)—again under the same reaction conditions as in process (A)—to give a mixture of the isomeric pyrimidine derivatives of the general formulae (I) and (Ia)

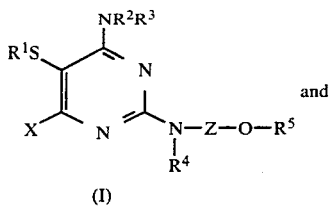

(I)

and

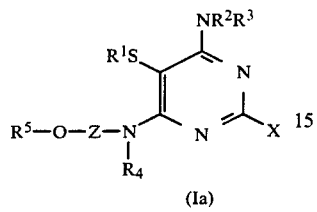

(Ia)

'wherein $R^1$, X, $R^2$, $R^3$, $R^4$, Z and $R^5$ have the above-mentioned meaning, and, finally, the desired isomers of the formula (I) are separated off.

It has furthermore been found that the new pyrimidine derivatives of the general formula (I) have powerful herbicidal properties.

Compared with the pyrimidines which are already known, the new pyrimidine derivatives (I) according to the invention are particularly distinguished structurally in that the 2-amino group is a straight-chain or branched alkoxyalkylamino group.

Surprisingly, the active compounds (I) according the invention are clearly more active than the pyrimidine derivatives already known, whilst having the same tolerance for maize and wheat. In particular, it has been found that the active compounds according to the invention have a considerably better action against Panicum, Chenopodium, Poa and Setaria than 2,4-diamino-6-chloro-5-methylthiopyrimidine, which is already known.

It has furthermore been found that the pyrimidine derivatives according to the invention also have powerful fungicidal properties at low concentrations which are not appropriate for herbicidal use.

Preferred pyrimidine derivatives of the formula (I) according to the invention are those in which X represents chlorine or fluorine, $R^1$ represents alkyl which has 1 to 6 C atoms and is optionally substituted by chlorine and/or fluorine, $R^2$, $R^3$ and $R^4$ in each case independently of one another represent hydrogen or alkyl with 1 to 6 C atoms, additionally $R^3$ represents ($C_1$-$C_6$)-alkoxy-($C_1$-$C_6$)-alkyl, Z represents a branched or straight-chain alkylene group with 2 to 10 C atoms and $R^5$ represents alkyl with 1 to 6 C atoms.

From this group of substances, compounds of the formula (I) which are particularly preferred are those in which X represents chlorine or fluorine, $R^1$ represents alkyl which has 1 to 4 C atoms and is optionally substituted by fluorine, $R^2$, $R^3$ and $R^4$ in each case independently of one another represent hydrogen or alkyl with 1 to 4 C atoms, additionally $R^3$ represents ($C_1$-$C_4$)-alkoxy-($C_1$-$C_4$)-alkyl, Z represents a branched or straight-chain alkylene group with 2 to 7 C atoms and $R^5$ represents alkyl with 1 to 4 C atoms.

If, for example, 2,4,6-trichloro-5-methylthiopyrimidine and 3-isopropoxypropylamine are used as starting substances according to process (A), and the 4,6-dichloro-2-(3-isopropoxypropylamino)-5-methylthio-pyrimidine thereby formed is further reacted with ammonia, the course of the reaction can be represented in summary form by the following equation:

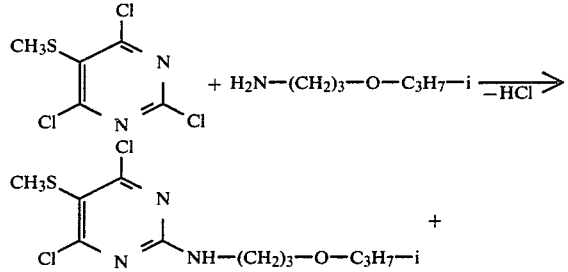

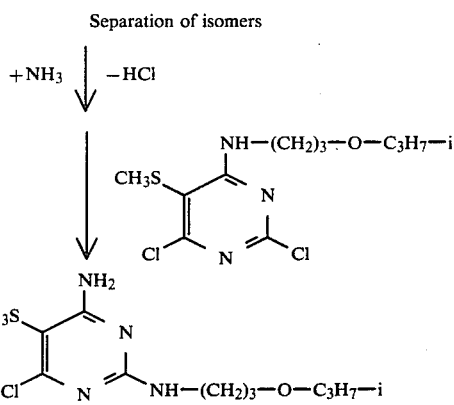

If, for example, 2,4,6-trifluoro-5-methylthiopyrimidine and ammonia are used as starting substances according to process (B), and the 4-amino-2,6-difluoro-5-methylthio-pyrimidine thereby formed is reacted with 3-methoxypropylamine, the course of the reaction can be represented in summary form by the following equation:

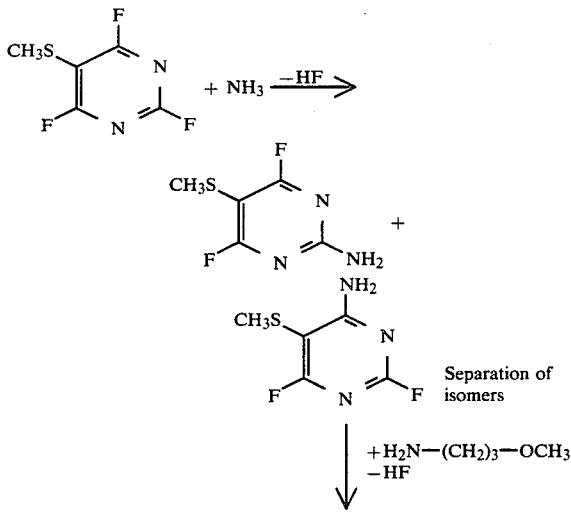

-continued

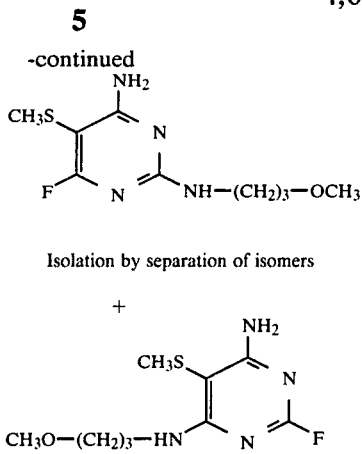

Isolation by separation of isomers

+

Formula (II) provides a general definition of the trihalogenopyrimidines used as starting substances. In this formula, $R^1$ and X preferably or particularly preferably represent those radicals which have already been mentioned as preferred or particularly preferred for these substituents in the description of the substances of the formula (I) according to the invention. The trihalogenopyrimidines of the formula (II) are known in some cases (X=Cl: French Patent Specification No. 1,549,494), or they can be prepared by known processes.

Formulae (III) and (V) provide general definitions of the amines also used as starting substances. In these formulae, $R^2$, $R^3$, $R^4$, $R^5$ and Z preferably or particularly preferably represent those radicals which have already been mentioned as preferred or particularly preferred for these substituents in the description of the substances of the formula (I) according to the invention. The amines of the formulae (III) and (V) are known, or they can be prepared by known processes in a manner analogous to that for the known compounds (compare, for example, Houben-Weyl, Methoden der organischen Chemie (Methods of Organic Chemistry), Volume XI/1, page 548, page 561 et seq., 4th edition 1957).

Possible diluents for the process according to the invention are organic solvents and water. Preferred organic solvents are hydrocarbons, such as toluene, aliphatic ketones, such as acetone, methyl ethyl ketone and diethyl ketone, and cycloaliphatic ethers, such as tetrahydrofuran or dioxane. Mixtures of various organic solvents and mixtures of water-miscible organic solvents with water are also suitable diluents.

The process according to the invention is carried out using acid-binding agents. Particularly suitable acid-binding agents are alkaline earth metal and alkali metal hydroxides, such as calcium hydroxide, sodium hydroxide or potassium hydroxide, and furthermore ammonia and tertiary aliphatic amines, such as, for example, triethylamine, as well as amine starting substance (III) or (V) employed in excess.

The reaction temperatures can be varied within a substantial range in the process according to the invention. The first process stage is in general carried out at temperatures from −30° to +150° C., preferably from −20° to +30° C.; the second process stage is in general carried out at 80° to 150° C., preferably at 90° to 130° C.

The reaction is carried out in the pressure range from 1 to about 10 bar.

In carrying out the process according to the invention, in general 1 to 1.1 moles of amine of the formula (III) or (V) and 1 to 1.2 moles of acid-binding agent, it being possible to use the amine (III) or (V) as the acid-binding agent, per mole of trihalogenopyrimidine of the formula (II) are employed in the first stage. The reaction is preferably carried out in a stoichiometric molar ratio. Similar statements apply to the second process stage.

The isomer mixtures obtained in both process stages can be separated in a simple manner by known methods, in particular by recrystallisation (compare, for example, French Patent No. A-2,119,234), so that the particular isomers desired can be isolated in a sufficiently pure form.

The active compounds according to the invention can be used as defoliants, desiccants, agents for destroying broad-leaved plants and, especially, as weedkillers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:
Dicotyledon weeds of the genera:
  Sinapsis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.
Dicotyledon cultures of the genera:
  Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.
Monocotyledon weeds of the genera:
  Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.
Monocotyledon cultures of the genera:
  Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, but orchards, banana plantations, coffee plantations, tea plantations, rubber plantations, oil palm plantations, cocoa plantations, soft fruit plantings and hopfields, and for the selective combating of weeds in annual cultures.

The active compounds according to the invention can be used—especially when applied by the post-emergence method—for selectively combating weeds in monocotyledon crops, for example in maize and cereals. The new active compounds are clearly more active than the compound 2,4-diamino-6-chloro-5-methylthiopyrimidine, which is already known, whilst having the same tolerance for maize and cereals.

The active compounds according to the invention also exhibit a powerful microbicidal action and can be employed in practice for combating undesired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

The good toleration, by plants, of the active compounds, at the concentrations required for combating plant diseases, permits treatment of above-ground parts of plants, of vegetative propagation stock and seeds, and of the soil.

As plant protection agents, the active compounds according to the invention can be used with particularly good success for systemic combating of rice diseases, such as Pyricularia oryzae.

The active compounds can be converted to the customary formulations, such as solutions, emulsions, suspensions, powders, foams, pastes, granules, aerosols, very fine capsules in polymeric substances and in coating compositions for seed, as well as ULV formulations.

These formulations are produced in a known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: auomatics, such as xylene, toluene or alkyl naphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silicic acid, alumina and silicates, as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers. Such as polyoxyethylene-fatty acid esters, polyoxyethylene-fatty alcohol ethers, for example alkylaryl polyglycol ethers, alkylsulphonates, alkylsulphates, arylsulphonates as well as albumin hydrolysation products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalin and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention, as such or in the form of their formulations, can also be used, for combating weeds, as mixtures with known herbicides, finished formulations or tank mixes being possible.

Possible components of the mixtures for heribicidal use are: ureas (for example Methabenzthiazuron); diphenyl ethers and acetanilides (for example Alachlor and Metolachlor); phenoxyalkanecarboxylic acids (for example 2,4-D, 2,4-DP, MCPA, MCPP and derivatives thereof); aryloxy- and hetaryloxy-phenoxypropionic acids (for example trimethylsilylmethyl 2-[4-(3,5-dichloro-2-pyridyloxy)-phenoxy]-propionate; (2,2-diethoxy)-ethyl 2-[4-(3,5-dichloro-2-pyridyloxy)-phenoxy]-propionate; and (2-benzyloxy)-ethyl 2-[4-(3,5-dichloro-2-pyridyloxy)-phenoxy]-propionate); triazines (for example Atrazine and Simazine); triazinones (for example Metribuzin and 4-amino-6-tert.-butyl-3-ethylthio-1,2,4-triazin-5(4H)-one); and triazinediones (for example Ametridione).

Mixtures with other known active compounds, such as fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomising, scattering, immersion, misting, vapourising, injecting, forming a slurry, brushing on, dusting, dry dressing, moist dressing, wet dressing, slurry dressing or encrusting.

When used as herbicides, the active compounds according to the invention can be applied either before or after emergence of the plants. They are preferably applied after emergence of the plants, that is to say by the post-emergence method. They can also be incorporated into the soil before sowing.

The amount of active compound applied can vary within a substantial range. It depends essentially on the nature of the desired effect. In general, the amounts applied for use as a herbicide are between 0.01 and 10 kg of active compound per ha, preferably between 0.05 and 5 kg per ha.

In the treatment of seed, amounts of active compound of 0.001 to 50 g per kilogram of seed, preferably 0.01 to 10 g, are generally required.

For the treatment of soil for fungicidal use, active compound concentrations of 0.00001 to 0.1% by weight, preferably 0.0001 to 0.02% by weight, are required at the place of action.

The following examples serve to further illustrate the invention.

PREPARATION EXAMPLES

Example 1

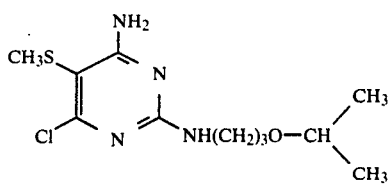

4-Amino-2-(3-isopropoxypropylamino)-6-chloro-5-methylthiopyrimidine/by process (A)

(a) 4,6-Dichloro-2-(3-isopropoxypropylamino)-5-methylthiopyrimidine/1st stage:

68.5 g (0.3 mole) of 2,4,6-trichloro-5-methylthiopyrimidine are dissolved in 300 ml of toluene. 30.3 g (0.3 mole) of triethylamine and 35.1 g (0.3 mole) of isopropoxypropylamine are added dropwise at 0° C. After the mixture had been subsequently stirred at room temperature for 1 hour, it is diluted with 500 ml of toluene and the organic phase is washed with water. After drying over sodium sulphate and removal of the solvent in vacuo, the resulting residue is stirred with 100 ml of petroleum ether, filtered off with suction, rinsed with petroleum ether and dried. 25.3 g (27.2% of theory) of the above-mentioned pyrimidine, melting point: 88° C., are thus obtained.

(b) 4-Amino-2-(3-isopropoxypropylamino)-6-chloro-5-methylthio-pyrimidine/2nd stage:

100 g (0.322 mole) of 4,6-dichloro-2-(3-isopropoxypropylamino)-5-methylthio-pyrimidine are dissolved in 400 ml of methanol and the solution is heated at 100° C. with 500 ml of ammonia in an autoclave for 3 hours. The undissolved residue is filtered off. After the methanol phase has been concentrated, the residue which remains is taken up in methylene chloride, the mixture is washed with water and the resulting organic phase is dried. After removal of the solvent, the resulting oil is stirred with petroleum ether. The crystals thereby obtained are filtered off with suction. 81 g (87% of theory) of the desired pyrimidine, melting point: 76° C., are obtained.

Example 2

4-Amino-2-(3-methoxypropylamino)-6-fluoro-5-methylthiopyrimidine/by process (B)

(a) 2,6-Difluoro-4-amino-5-methylthio-pyrimidine/1st stage:

9 g (0.05 mole) of 2,4,6-trifluoro-5-methylthiopyrimidine are dissolved in 200 ml of toluene. 6.8 g (0.1 mole) of 25% strength aqueous ammonia solution are added dropwise at −30° C. and the mixture is stirred at −30° C. for four hours and warmed to room temperature. After addition of 300 ml of water, the precipitate formed (product A) is filtered off with suction. The toluene phase is separated off and the resulting aqueous phase is extracted twice with 100 ml of toluene. The combined organic phases are dried over sodium sulphate and the solvent is then stripped off. A white solid (product B) results.

Product A: Yield: 1.6 g (18%), melting point: 245° C., 2,6-difluoro-4-amino-5-methylthio-pyrimidine;

Product B: Yield: 3.5 g (40%), melting point: 118° to 121° C., 4,6-difluoro-2-amino-5-methylthiopyrimidine.

In larger batches (about 1 mole), the isomers are obtained in an overall yield of 75%.

(b) 4-Amino-2-(3-methoxypropylamino)-6-fluoro-5-methylthio-pyrimidine (isomer mixture)/2nd stage:

5 g (0.028 mole) of 2,6-difluoro-4-amino-5-methylthio-pyrimidine (product A) are boiled under reflux in 100 ml of dioxane at 80° C. with 5 g (0.056 mole) of 3-methoxypropylamine for three hours. After the reaction mixture has been cooled to room temperature, it is poured into 1.5 l of ice-water and extracted with methylene chloride. After drying over $Na_2SO_4$ and concentration, 4.2 g (61% of theory) of a mixture of 4-amino-2-(3-methoxypropylamino)-6-fluoro-5-methylthio-pyrimidine and 4-amino-6-(3-methoxypropylamino)-2-fluoro-5-methylthio-pyrimidine, melting point: 48° to 64° C., are obtained.

The pyrimidine derivatives of the general formula (I)

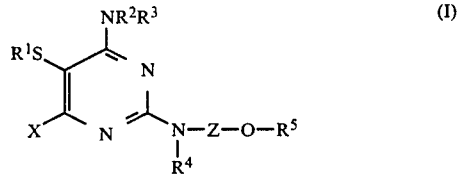

mentioned in the following Table 1 have been prepared by an analogous route.

TABLE 1

| Example No. | X | $R^1$ | $R^2$ | $R^3$ | $R^4$ | Z | $R^5$ | Physical constants |
|---|---|---|---|---|---|---|---|---|
| 3 | Cl | $CH_3$ | H | $CH_3$ | H | $-(CH_2)_3-$ | i-$C_3H_7$ | Mp. 68–71° C. |
| 4 | Cl | $CH_3$ | $CH_3$ | $CH_3$ | H | $-(CH_2)_3-$ | i-$C_3H_7$ | $n_D^{20}$ 1.5662 |
| 5 | Cl | $CH_3$ | H | $C_2H_5$ | H | $-(CH_2)_3-$ | i-$C_3H_7$ | Mp. 51–53° C. |
| 6 | Cl | $CH_3$ | H | n-$C_3H_7$ | H | $-(CH_2)_3-$ | i-$C_3H_7$ | Mp. 55–58° C. |
| 7 | Cl | $CH_3$ | H | i-$C_3H_7$ | H | $-(CH_2)_3-$ | i-$C_3H_7$ | Mp. 55–57° C. |
| 8 | Cl | $CH_3$ | H | n-$C_4H_9$ | H | $-(CH_2)_3-$ | i-$C_3H_7$ | Mp. 30° C. |
| 9 | Cl | $CH_3$ | H | H | H | $-(CH_2)_3-$ | $CH_3$ | Mp. 116° C. |
| 10 | Cl | $CH_3$ | H | $CH_3$ | H | $-(CH_2)_3-$ | $CH_3$ | Mp. 93° C. |
| 11 | Cl | $CH_3$ | $CH_3$ | $CH_3$ | H | $-(CH_2)_3-$ | $CH_3$ | Mp. 58° C. |
| 12 | Cl | $CH_3$ | H | $C_2H_5$ | H | $-(CH_2)_3-$ | $CH_3$ | Mp. 98° C. |
| 13 | Cl | $CH_3$ | H | n-$C_3H_7$ | H | $-(CH_2)_3-$ | $CH_3$ | Mp. 76° C. |
| 14 | Cl | $CH_3$ | H | i-$C_3H_7$ | H | $-(CH_2)_3-$ | $CH_3$ | Mp. 68° C. |
| 15 | Cl | $CH_3$ | H | $-(CH_2)_3OCH_3$ | H | $-(CH_2)_3-$ | $CH_3$ | Mp. 56° C. |
| 16 | F | $CH_3$ | H | H | H | $-(CH_2)_3-$ | $C_2H_5$ | Isomer mixture: $n_D^{20}$: 1.54 |

TABLE 1-continued

| Example No. | X | R$^1$ | R$^2$ | R$^3$ | R$^4$ | Z | R$^5$ | Physical constants |
|---|---|---|---|---|---|---|---|---|
| 17 | F | CH$_3$ | H | H | H | —(CH$_2$)$_2$— | CH$_3$ | Isomer mixture: Mp. 86–88° C. |
| 18 | F | CH$_3$ | H | —(CH$_2$)$_3$OCH$_3$ | H | —(CH$_2$)$_3$— | CH$_3$ | Isomer mixture: n$_D^{20}$: 1.5444 |
| 19 | Cl | CH$_3$ | H | H | H | —(CH$_2$)$_3$— | C$_2$H$_5$ | Mp. 100–104° C. |
| 20 | Cl | CF$_3$ | H | H | H | —(CH$_2$)$_3$— | i-C$_3$H$_7$ | Isomer mixture: Mp. 124–142° C. |
| 21 | Cl | CF$_3$ | H | H | H | —CH—(CH$_2$)$_2$—<br>\|<br>CH$_3$ | CH$_3$ | Mp. 73–75° C. |
| 22 | Cl | CH$_3$ | H | H | H | —(CH$_2$)$_2$— | CH$_3$ | Mp. 120–122° C. |
| 23 | Cl | CH$_3$ | H | —CH$_2$—C$_4$H$_9$—t | H | —(CH$_2$)$_3$— | i-C$_3$H$_7$ | Mp. 90–92° C. |

Starting substances:

The trihalogenopyrimidines (II-1) and II-3) used as starting substances and the dichloropyrimidine derivative (VIb-1) and their preparation are known:

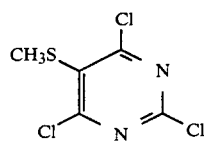

(II-1) known from French Patent A-1,549,494; and J. Medicinal Chem. 18, pages 553–8 (1975)

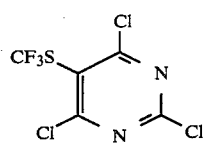

(II-3) known from M. Lieb, Dissertation, University of Bochum 1980

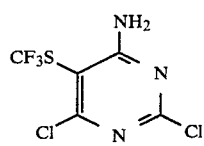

(VIb-1) known from M. Lieb, Dissertation, University of Bochum 1980

The 2,4,6-trifluoro-5-methylthio-pyrimidine (II-2) which has not previously been described, can be prepared from (II-1) as follows:

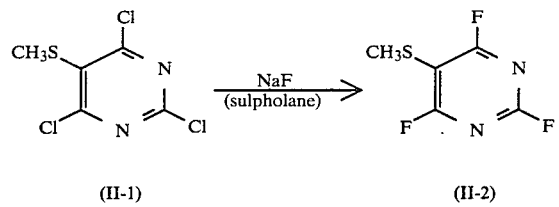

824 g (19.62 moles) of sodium fluoride and 1,430 ml of sulpholane are introduced into a 4 liter vessel with ground glass joints, provided with a distillation bridge; about 250 ml of sulpholane are distilled off at 145° C./20 mbar. 750 g (3.27 moles) of 2,4,6-trichloro-5-methylthiopyrimidine (II-1) are then added and the mixture is stirred at 200° C. for 4 hours. The reaction mixture is then distilled over the bridge. The following fractions are obtained by redistillation over a 50 cm packed column:

(a) 483 g of 2,4,6-trifluoro-5-methylthio-pyrimidine (II-2) (=82.1% of theory) of boiling point 72°–73° C./20 mbar, n$_D^{20}$: 1.4876;

(b) 37 g of last runnings, boiling range: 75°–120° C./20 mbar; n$_D^{20}$: 1.5211.

Residue: 180 g of sulpholane (=tetramethylenesulphone).

In general, 6 moles of NaF are employed per mole of 2,4,6-trichloro-5-methylthio-pyrimidine and 60 ml of sulpholane are employed per mole of NaF.

Use Examples

The compounds shown below were used as comparison substances in the following use examples:

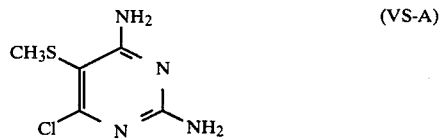

(known from European Patent A-0,000,681, Example 12);

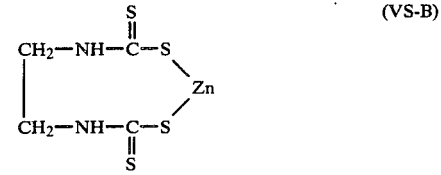

Zinc ethylene-1,2-bis(dithiocarbamate); common name: Zineb (known, for example, from R. Wegler "Chemie der Pflanzenschutz- und Schädlingsbekämpfungsmittel" ("Chemistry of the Plant Protection Agents and Agents for Combating Pests"), Springer Verlag 1970, Volume 2, page 65 et seq.).

Example A

Post-emergence test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of the active compound in such a way as to apply the particular amounts of active compound desired per unit area. The concentration of the spray liquor is so chosen that the particular amounts of active compound desired are applied in 2,000 l of water/ha. After three weeks, the degree of damage to the plants is rated in % damage in comparison to the development of the untreated control. The figures denote:

0%=no action (like untreated control)
100%=total destruction

In this test, a clearly superior activity compared with the prior art is shown, for example, by the compounds according to the following preparation examples: 1.

Example B

Pyricularia test (rice)/protective
Solvent: 12.5 parts by weight of acetone
Emulsifier: 0.3 parts by weight of alkylaryl polyglycol ether To produce a suitable preparation of active compound, 1 part by weight of active compound is mixed with the stated amount of solvent, and the concentrate is diluted with water and the stated amount of emulsifier, to the desired concentration.

To test for protective activity, young rice plants are sprayed with the preparation of active compound until dripping wet. After the spray coating has dried on, the plants are inoculated with an aqueous spore suspension of Pyricularia oryzae. The plants are then placed in a greenhouse at 100% relative atmospheric humidity and 25° C.

Evaluation of the disease infestation is carried out 4 days after the inoculation.

In this test, a clearly superior activity compared with the prior art is shown, for example, by the compounds according to the following preparation examples: (13), (14), (16) and (19).

Example C

Pyricularia test (rice)/systemic
Solvent: 12.5 parts by weight of acetone
Emulsifier: 0.3 parts by weight of alkylaryl polyglycol ether To produce a suitable preparation of active compound, 1 part by weight of active compound is mixed with the stated amount of solvent, and the concentrate is diluted with water and the stated amount of emulsifier, to the desired concentration.

To test for systemic properties, standard soil in which young rice plants have been grown is watered with 40 ml of the preparation of active compound. 7 days after the treatment, the plants are inoculated with an aqueous spore suspension of Pyricularia oryzae. Thereafter, the plants remain in a greenhouse at a temperature of 25° C. and a relative atmospheric humidity of 100% until they are evaluated.

Evaluation of the disease infestation is carried out 4 days after the inoculation.

In this test, a clearly superior activity compared with the prior art is shown, for example, by the compounds according to the following preparation examples: (14) and (16).

We claim:

1. A method of combating fungi which comprises administering to such fungi or to a fungus habitat a fungicidally effective amount of 2-,4-diamino-6-halogeno-5-alkylthiopyrimidine of the formula

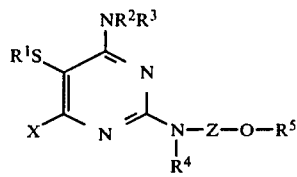

wherein
X is halogen,
R$^1$ is alkyl which has 1 to 6 C atoms and which is optionally substituted by halogen,
R$^2$ is hydrogen or alkyl with 1 to 6 C atoms,
R$^3$ is hydrogen, alkyl or alkoxyalkyl with 1 to 6 C atoms in each alkyl moiety,
R$^4$ is hydrogen or alkyl with 1 to 6 C atoms,
Z is a branched or straight-chain alkylene group with 2 to 10 C atoms, and
R$^5$ is alkyl with 1 to 6 C atoms.

2. A method according to claim 1, in which
X is chlorine or fluorine, and
R$^1$ is alkyl with 1 to 6 C atoms optionally substituted by at least one of chlorine and fluorine.

3. A method according to claim 1,
in which
X is chlorine or fluorine,
R$^1$ is alkyl which has 1 to 4 C atoms and is optionally substituted by fluorine,
R$^2$, R$^3$ and R$^4$ each independently is hydrogen or alkyl with 1 to 4 C atoms, and additionally R$^3$ may be (C$_1$-C$_4$)-alkoxy-C$_1$-C$_4$)-alkyl,
Z is an alkylene group with 2 to 7 C atoms, and
R$^5$ is alkyl with 1 to 4 C atoms.

4. A method according to claim 1, wherein such compound is 4-amino-2-(3-isopropoxyporpylamino)-6-chloro-5-methylthio-pyrimidine of the formula

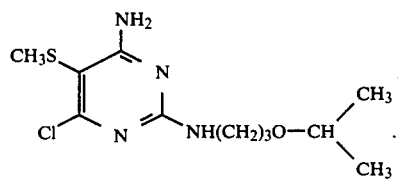

5. A method according to claim 1, wherein such compound is 4-isopropylamino-2-(3-methoxypropylamino)-6-chloro-5-methylthio-pyrimidine of the formula

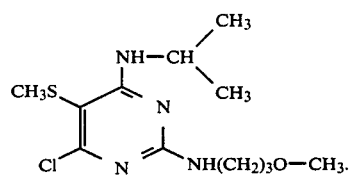

6. A method according to claim 1, wherein such compound is 4-amino-2-(3-ethoxypropylamino)-6-fluoro-5-methylthio-pyrimidine of the formula

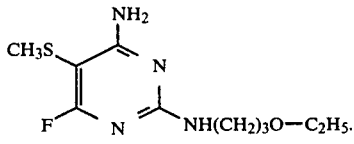

* * * * *